US 6,645,185 B2

(12) United States Patent
Bird et al.

(10) Patent No.: US 6,645,185 B2
(45) Date of Patent: Nov. 11, 2003

(54) BAND FOR ANCHORING TUBULAR DEVICE TO THE BODY

(75) Inventors: John R. Bird, St. Paul, MN (US); Michael J. Frazer, Minneapolis, MN (US)

(73) Assignee: Bird & Cronin, Eagan, MN (US)

( * ) Notice: Subject to any disclaimer, the term of this patent is extended or adjusted under 35 U.S.C. 154(b) by 0 days.

(21) Appl. No.: 09/848,708

(22) Filed: May 3, 2001

(65) Prior Publication Data

US 2002/0165495 A1 Nov. 7, 2002

(51) Int. Cl.[7] .................................................. A61F 5/44
(52) U.S. Cl. ...................................... 604/345; 604/179
(58) Field of Search ................................ 604/174, 175, 604/179, 180, 345; 128/DIG. 26

(56) References Cited

U.S. PATENT DOCUMENTS

| 2,449,882 A | | 9/1948 | Daniels ........................ 604/179 |
| 3,389,160 A | | 6/1968 | Reid |
| 3,726,280 A | | 4/1973 | Lacount ....................... 604/179 |
| 3,773,048 A | * | 11/1973 | Kirkliauskas ............... 128/283 |
| 3,804,699 A | * | 4/1974 | Johnson ........................ 161/39 |
| 3,878,849 A | | 4/1975 | Muller et al. ................ 604/179 |
| 3,930,497 A | * | 1/1976 | Krebs et al. ................. 128/132 |
| 4,088,136 A | | 5/1978 | Hasslinger et al. .......... 604/179 |
| 4,096,863 A | | 6/1978 | Kaplan et al. ............... 604/179 |
| 4,445,894 A | | 5/1984 | Kovacs ........................ 604/179 |
| 4,569,348 A | | 2/1986 | Hasslinger ................... 604/179 |
| 4,591,356 A | | 5/1986 | Christie ....................... 604/179 |
| 5,352,209 A | | 10/1994 | Bird et al. ................... 604/179 |
| 5,891,977 A | | 4/1999 | Dietz et al. |
| 5,998,331 A | | 12/1999 | Policello |
| 6,001,140 A | | 12/1999 | Grabowski et al. |

FOREIGN PATENT DOCUMENTS

| DE | 43 18 537 | 12/1994 |
| EP | 0 535 596 | 4/1993 |

OTHER PUBLICATIONS

Sandbrink et al., Pest. Sci., 38, 272–273 (1993).
Snow et al., Langmuir, 9, 424–430 (1993).

* cited by examiner

Primary Examiner—Manuel Mendez
(74) Attorney, Agent, or Firm—Merchant & Gould P.C.

(57) ABSTRACT

An improved anchoring appliance for detachably securing a catheter or other elongate or tube-like member to the limb of a body is disclosed. A primary strap with a slip-resistant surface portion is configured for adjustable encircling attachment to the limb. The slip-resistant surface portion directly engages the limb and includes material that resists slippage of the strap longitudinally along the limb. A secondary anchoring member attached to the strap is configured to detachably retainably engage and hold a catheter or other elongate or tube-like member in a desired position relative to the strap. The anchoring appliance preferably has at least its slip-resistant surface portion made of non-allergenic materials.

15 Claims, 3 Drawing Sheets

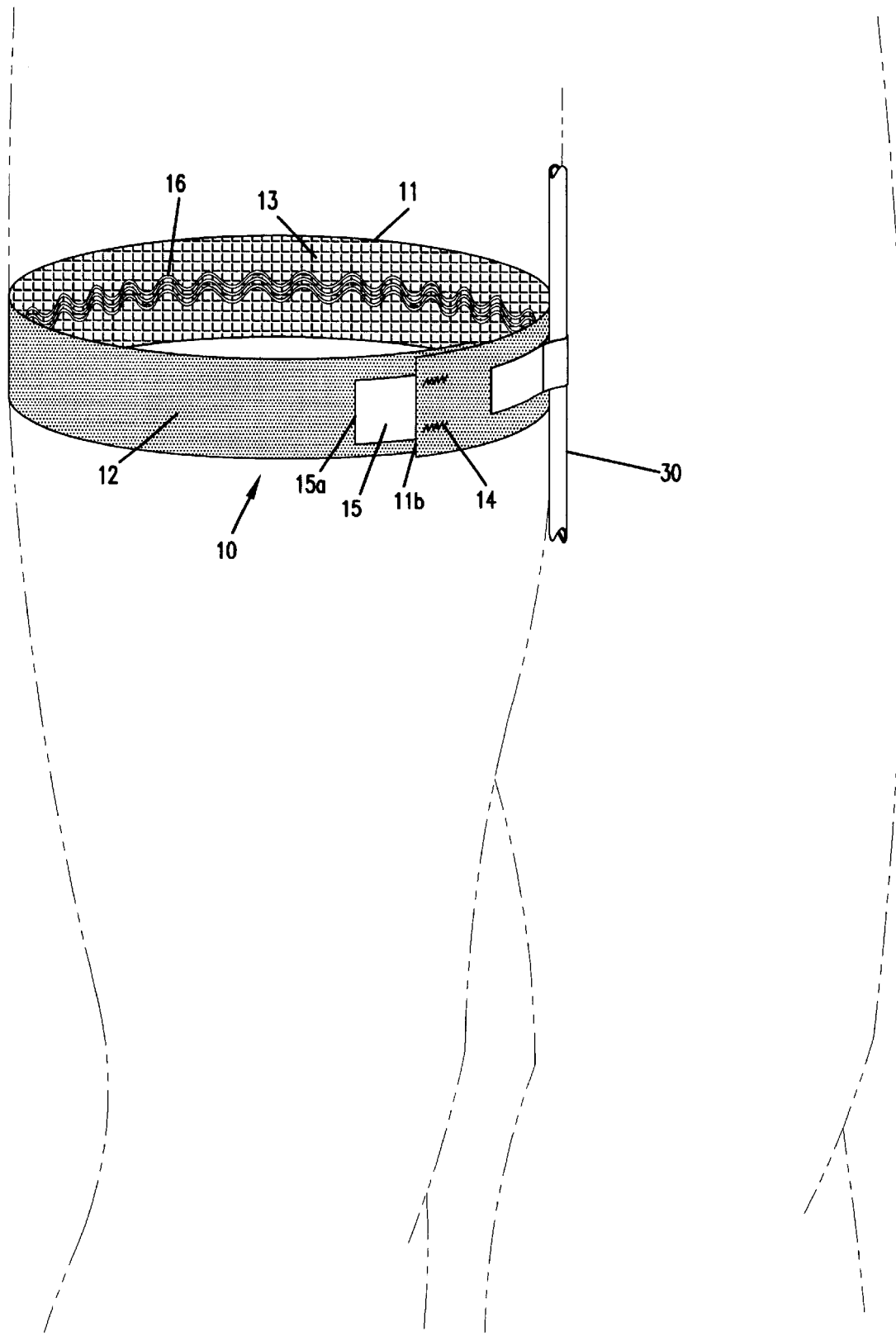

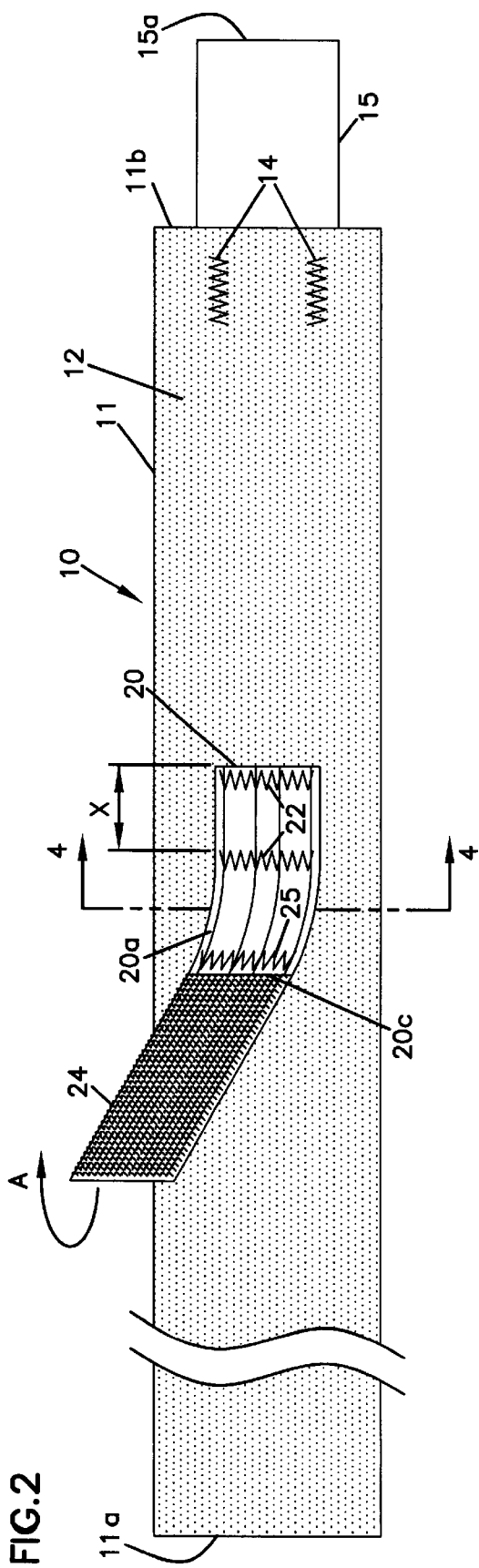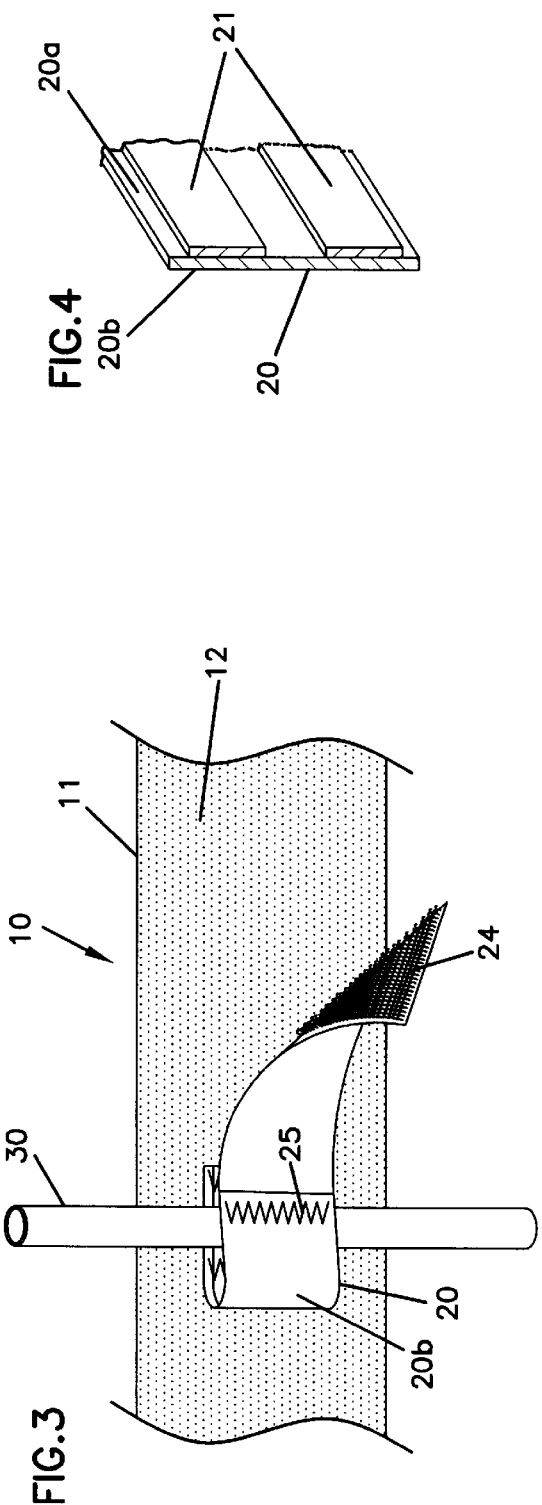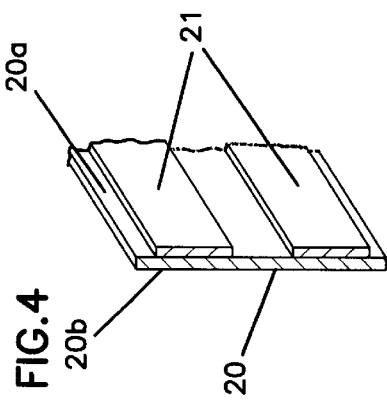

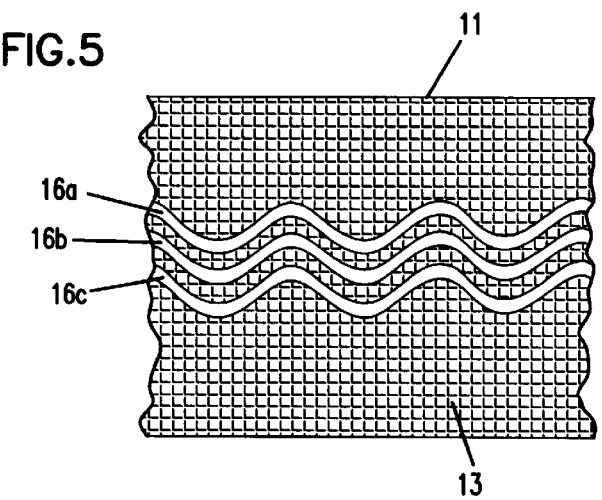
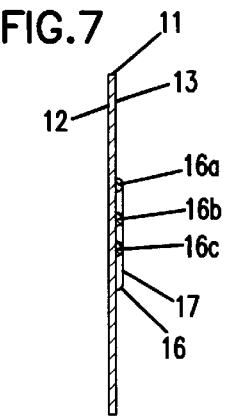
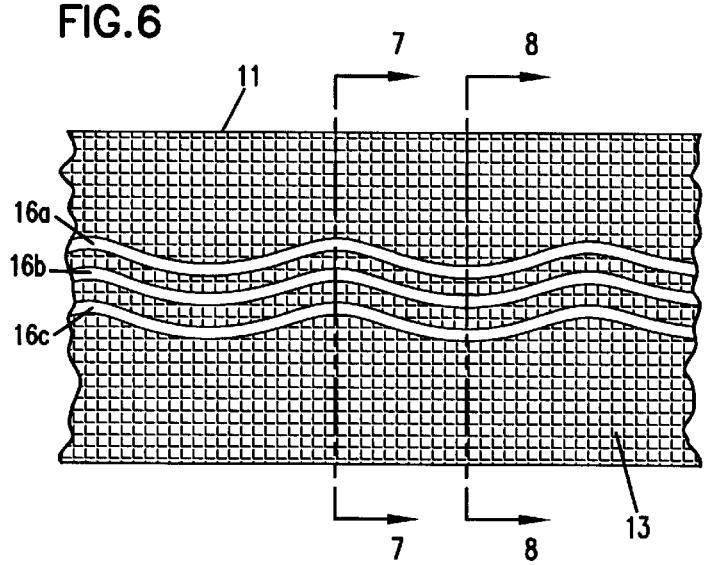
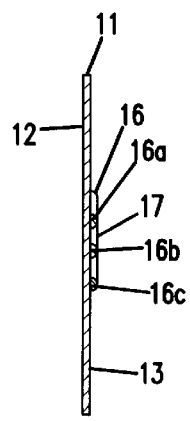
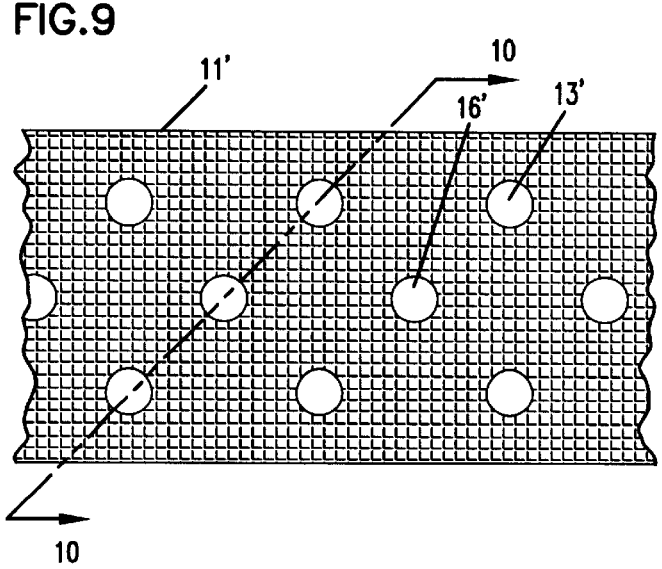
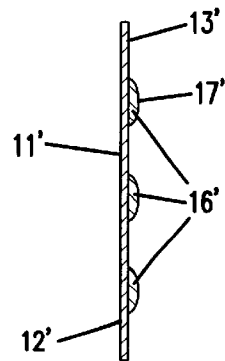

BAND FOR ANCHORING TUBULAR DEVICE TO THE BODY

FIELD OF THE INVENTION

This invention relates generally to medical accessories and more particularly to an apparatus for securing a catheter or other tube-like member to a limb or trunk body portion of a human.

CROSS-REFERENCE TO RELATED PATENTS

My U.S. Pat. No. 5,352,209 entitled Band For Anchoring A Tubular Device to the Body is herein incorporated by reference.

BACKGROUND OF THE INVENTION

There are many instances in which it is desirable to retain or hold a tube-like member in generally fixed position relative to a limb, such as an arm or leg of a human. The most obvious need arises in hospitals or other patient care facilities. However, any number of situations exist wherein it is necessary or preferable for an elongate member such as for example a rod, cord or tube to be maintained in a fixed or secure position relative to the body so as not to become caught or snagged during movement or activity, or so as not to slip into a position wherein the tube could be bent or crimped or otherwise damaged.

Examples of such applications might include patient-care catheter tubes or intravenous tubes. Such tubes must be positioned so as not to be bent, pinched, crushed, snagged or pulled by movement of the patient or by those administering to the patient.

A number of techniques and apparatus have been used in the past to address the problem. The tube can be directly taped to the patient. However, such taping is not particularly comfortable to the patient and does not lend itself for a lead to replacement or servicing of the tube. Besides, the tape can leave undesirable residue on the tube and on the patient's body. Taping can also cause allergic skin reaction, pain upon removal, tape burn and/or hair loss.

A commonly used non-tape retainer has been an adjustable strap member configured for attachment to the leg or arm of the patient, as described in U.S. Pat. No. 4,096,863. The retaining band of such structure includes a rigid metal clip or buckle through which a secondary strip of material passes, to form a loop that can be retainably tightened around a catheter tube or the like, for holding the tube in position against the band. Such structure provides improved flexibility for use with patients of varied size limbs and for use with tubes of varied outer circumferences. However, the rigid clip or buckle of such device adds to the cost of the device, and permits slippage of the tube relative to the strap if not tightened enough, or undesirable bending and restriction of the tube, if tightened too much. Further, the presence of the rigid metal clip can cause discomfort to the wearer and can be difficult to secure since the tube retaining tab must be threaded through the clip or buckle in order to secure the tube.

An improved retaining strap that solves the above problems is disclosed in my prior U.S. Pat. No. 5,352,209. That strap eliminated the metal clip or buckle of the prior art, which made it easier to manufacture, less expensive, easier to use, more comfortable to the patient and minimized the potential of damage to or bending or crimping of the tube being held thereby.

The retaining straps of the prior art, however, all generally suffer from a common shortcoming. They have a tendency when operatively positioned at a comfortable tension on a limb, such as on an arm or leg of a patient, to slip or slide relative to the limb as the patient moves or as a result of pressure being applied to the strap or to the tube being retained thereby. Such strap movement relative to the limb can result in tugging or pulling on the retained tube, causing discomfort or injury to the patient. One solution to such slippage may be to tighten the straps to the limb with such force that it would not slip. However, such tension might be so high as to cause discomfort to the patient or constriction in the patient's limb. Another problem associated with some of the prior art retaining devices is that they have used materials such as latex in their construction, which could cause allergic reactions to patients and users of the straps.

The present invention addresses these shortcomings of prior art retaining devices and generally provides an improvement over such prior art devices while maintaining the advantages provided by my prior patented retaining strap. This invention provides a retaining strap resists sliding movement or slippage relative to the patient's body once operatively positioned on the body, and which is preferably constructed of non-allergenic materials. The device requires less tension and tightening of the strap on the limb which minimizes constriction, resulting in improved blood circulation and increased patient comfort.

SUMMARY OF THE INVENTION

This invention provides a very user friendly and efficient retainer strap or band for holding an elongate member such as a tubular device in place relative to a limb or body member of a patient, which is also very comfortable to the patient. The present invention uses no buckles for providing the retaining function and does require the retaining member to be passed or inserted through any holes or slots in the band or strap structure in order to accomplish the retaining function. The tube retaining or holding mechanism is carried by a primary band or strap that incorporates and infinitely adjustable hook and loop fastener technique which permits the primary band to be sized upon application to the patient, to the unique size and shape of the body member to which it is being applied. The primary support band includes an elastic portion which enables the band to be secured at the proper tension, as dictated by the patient to which it is being secured. Such tension is enough to hold the band in place on the limb, but which is also comfortable to the patient and which doesn't adversely constrict blood flow through the limb. The primary support band includes a slip-resistant inner surface for contacting the wearer's skin that minimizes slippage or sliding of the support band once placed in operative position relative to the wearer's body. Once the primary support band has been properly positioned on the limb or body member of the patient, the tube member to be secured is simply seated upon a frictional material of the tube retainer portion and is rapidly secured thereto by simple one-motion step which stretches the tube retaining material while placing it in secure engagement with the tube. The tube retaining strap portion is firmly retained in engagement with the tube by means of a hook and loop fastener tab that is sized for ease of handling by the attendant and for facilitating stretching of the retained material. The entire retainer strap is preferably constructed of non-allergenic materials that are safe for use by the wearer and/or those handling the retaining strap.

According to one aspect of the invention, there is provided an appliance for retaining an elongate member such as a catheter to a body portion of a person, comprising:

(a) a primary strap member configured to encircle the body portion to which a said elongate member is to be retained, said primary strap member having oppositely disposed outer and inner surfaces;

(b) a fastener system for releasably securing said primary strap member around and into snug engagement with said body portion; wherein said inner surface of said primary strap member cooperatively addresses said body portion;

(c) a slip-resistant material forming at least a portion of said inner strap surface and configured to engage said body portion; and (d) a secondary member secured to said primary strap member, configured to releasably secure an elongate object to said primary strap member.

According to a further aspect of the invention, the fastener system may comprise a hook and loop fastening system. According to yet another aspect of the invention, at least those portions of the appliance designed to contact the body portion comprise non-allergenic materials, and preferably contain no latex. According to yet a further aspect of the invention, the slip-resistant materials are configured to form an open pattern along the inner surface of the primary strap member to enable the passage of air or breathing through the primary strap material. According to one aspect of the invention, such slip-resistant material comprises silicone which can be configured to stretch with the primary strap member.

According to yet a further aspect of the invention, there is provided an appliance for releasably securing a tube-like member along a limb, comprising:

(a) a primary strap member configured to encircle the limb, said primary member being at least partially stretchable in a longitudinal direction and having at least a partially slip-resistant first surface;

(b) a first fastening system for securing said primary strap member in encircling manner about said limb, with said first surface engaging said limb;

(c) a second fastening system for releasably securing a tube-like member to said primary strap member; and (d) said slip-resistant first surface being arranged and configured to inhibit relative sliding motion between said primary strap member and said limb.

While the invention will be described with respect to its application for holding a catheter strap, the invention is not limited to such application. Further, while the invention will be described with respect to specific types of materials and with respect to particular sizes of the various components of the preferred embodiment, it will be understood that the invention is not to be sole limited to the described materials or to their preferred embodiment sizes. The invention will also be described with respect to particular preferred embodiments thereof, which illustrate the use of various slip-retardant materials and patterned configurations of such materials on the primary band member. It will be understood by those skilled in the art, that the invention is not to be limited by the particular types of slip-retardant materials described or to the particular patterns or configurations in which they are presented with respect to the preferred embodiments disclosed. These and other features of the invention and modifications thereof will become obvious to those skilled in the art in view of a more detailed description thereof.

BRIEF DESCRIPTION OF THE DRAWING

Referring to the Drawing, wherein like numerals represent like parts throughout the several views:

FIG. 1 is a fragmentary perspective view of a leg of a human, to which a preferred embodiment of the invention is secured and which illustrates the manner in which the invention may be used to secure a catheter along the leg;

FIG. 2 is a plan view of outer surface of the band shown in FIG. 1;

FIG. 3 is an enlarged prospective view of that portion of the band of FIG. 2 which engages the tube-like member to be retained thereby, illustrating the fold-over tab portion thereof as it is being retainably looped over the tube-like member;

FIG. 4 is a cross-sectional view of the fold-over tab portion of FIGS. 2 and 3, generally taken along the Line 4—4 of FIG. 2;

FIG. 5 is a fragmentary plan view of a first embodiment of a portion of the inner surface of the band shown in FIG. 2, illustrated in an unstretched configuration;

FIG. 6 is a plan view of the inner surface of the band of FIG. 5, illustrated in a stretched configuration;

FIG. 7 is a cross-sectional view of the band of FIG. 6, generally taken along the Line 7—7 of FIG. 6;

FIG. 8 is a cross-sectional view of the band of FIG. 6, generally taken along the Line 8—8 of FIG. 6;

FIG. 9 is a fragmentary plan view of a second embodiment of a portion of the inner surface of the band of FIG. 2, illustrating a different pattern of slip-resistant material than illustrated in FIG. 5; and FIG. 10 is a cross-sectional view of the band of FIG. 9, generally taken along the Line 10—10 of FIG. 9.

DETAILED DESCRIPTION OF THE INVENTION

The tube-retaining band or appliance of the present invention is generally illustrated at 10 in the figures. The band 10 has a primary strap portion 11 sized to encircle the limb or body portion of a person, to which a tube device 3 is to be secured. A leg or limb portion of a person is illustrated by phantom lines in FIG. 1. The primary strap 11 is preferably constructed of an elastic woven, knit, or webbing material which is commercially available. The strap 11 is stretchable in the longitudinal or lengthwise direction, but is generally inelastic or non-strechable across its width. In a preferred embodiment, the primary strap is configured from a knitted or woven elastic material having an elongation or "stretch" in the longitudinal direction of about 130 percent. In the preferred embodiment of the appliance, an outer surface 12 of the band, illustrated as the upper-most surface in FIG. 2 is configured as a looped material, typically or brushed nylon or knit or woven loop material having loops extending outwardly from the surface. The opposite or inner surface 13 of the primary strap 11 is configured to directly engage the skin of the limb or other member encircled by the primary strap 11. The inner surface 13 of the primary strap 11 is constructed of or may, or may not carry a soft lining material which may, for example, be in the form of a Helanca™ backing or other soft material which is comfortable and non-allergenic to the wearer's skin but which does not interfere with the lengthwise elasticity of the primary strap material. The primary strap 11, as well as all other portions of the appliance are preferably constructed of latex-free materials. For example, the primary strap material of the preferred embodiment has a latex-free content comprising approximately 28% elastic, 58% polyester and 14% nylon. Alternatively, the primary strap may be configured of multiple sections as described, for example, in my earlier U.S. Pat. No. 5,352,209, hereby incorporated by reference.

The dimensions of the primary strap 11 will be configured to accommodate the use to which the appliance 10 will be put. In a preferred embodiment application of the appliance for use in retainably holding a catheter tube or intravenous tube in position on a limb of a patient, the width of the primary strap is approximately two inches. Similarly, the length of the primary strap will vary depending upon the circumference of the limb or member it is intended to encircle. A typical adult catheter holder appliance may, for example, have a primary strap that extends from about 18 to 24 inches in length in an unstretched condition, and may longitudinally stretch at distance equal to 1.5 times its unstretched length.

The primary strap 11 extends between first and second ends 11a and 11b respectively. A 5A short strip 15 of "hook"-type fastener material similar to that as marketed under the Velcro® trademark, is secured by stitching 14 to the inner surface 13 of the primary strap 11 adjacent its second end 11b, and longitudinally extends outwardly therefrom to a distal end 15a. The hook members of the fastener material 15 extend outwardly from the inner surface 13 side of the primary strap (i.e. that surface of the fastener 15 opposite to the one shown in FIG. 2) such that when the primary strap is operatively wound in encircling manner around a limb, the soft lining material of the inner surface 13 addresses and engages the limb, beginning with the first end 11 a of the strap 11, and extending toward the second end 11 b and its attached fastener 15. The length of the strap 11 is sized such that the fastener material 15 does not come into direct contact with a limb, but overlaps and engages the loops of the outer surface 12 of the primary strap as the strap encircles the limb (as illustrated in FIG. 1), forming a hook and loop fastening system that circumferentially secures the primary strap to and in operative position along a limb of the wearer. When thus positioned, the hooks of the fastener material 15 releasably engage the loop members on the outer surface 12 of the primary strap 11.

Because the primary strap 11 is stretchable, an attendant can apply the primary strap portion to a patient with sufficient tension to that the patient's limb is firmly gripped by the primary strap 11 and held in place, but without applying so much pressure to the limb soas to cut off or harmfully impede circulation. Further, since the hook portion of the fastener 15 of the primary strap may be secured at any position along the outer looped material 12 of the strap 11, the primary strap portion 11 is continuously operatively adjustable along its length, as permitted by the longitudinal expansion of the primary strap material. Those skilled in the art will appreciate that while hook and loop fastener systems or configurations will be disclosed with reference to the preferred embodiments of the invention, other fastener systems could equally well be used within the scope of this invention.

A slip-resistant material such as silicone may be applied to the inner surface 13 of the primary strap 11 to prevent or retard slippage between the inner surface 13 of the primary strap 11 and the outer limb surface to which the primary strap is affixed. The slip resistant material may be uniformly applied across the inner surface 13 of the primary strap 11, or in varied configurations or may be woven into the strap 11. A first embodiment of a preferred configuration of the slip-resistant material is illustrated at 16 in the figures. The slip-resistant material 16 is illustrated in FIGS. 1, 5 and 6 in a configuration of a plurality of generally parallel curved strips or ribbons of material 16a–16c, longitudinally extending along the length of the inner surface 13 of the primary strap 11. Such strip configuration of the slip-resistant material 16 enhances the passage of air, or breathing, through the primary strap 11. Referring to the enlarged illustrations of the inner surface 13 of the strap 11 of FIGS. 5 and 6, in a preferred configuration, the slip-resistant material is applied to the inner surface and generally sinusoidal manner along the length of the primary strap 11. In a preferred embodiment of the invention, the slip-resistant material 16 is in the nature of silicone material; however, it will be understood by those skilled in the art that other materials such as for example, neoprene or latex rubber, could equally well be used. Further, it will be understood that the slip-resistant material 16 can be applied to the inner surface 13 of the primary strap ii in various other patterns and configurations such as, by way of example only, randomly or patterned configurations of dots or patches 16', such as illustrated in FIG. 9, or in any other configuration as limited only by the imagination and resources of the person and/or machine applying the slip-resistant material 16 to the strap. For ease of reference, the structures illustrated in FIG. 9 which are similar to those of FIGS. 1–8, have been illustrated by the same numerical designations used in FIGS. 1–8, followed by a prime (') designation. Alternatively, the slip-resistant material need not be applied in a separate application to the inner surface 13 of the primary strap 11, but may actually form an integral part of the primary strap 11 such as threads of neoprene or silicone type threaded material that is actually woven into and forms a part of the primary strap material in a manner such that portions thereof would be exposed at the inner surface 13 of the primary strap 11, thereby forming the slip-resistant function of the invention.

The slip-resistant material 16 is preferably elastic in nature so as to stretch and deform with the primary strap 11, as illustrated by the comparisons of FIGS. 5 and 6. FIG. 5 illustrates the inner surface 13 of the primary strap 11 when in an unstretched configuration; whereas FIG. 6 illustrates the same inner surface 13 of the primary strap 11 when in a longitudinally stretched configuration. The ribbons of slip-resistant material 16a–16c are illustrated as longitudinally stretching with the inner surface of the primary strap 11 while maintaining an exposed outer surface (generally indicated at 17 in the cross-sectional view of FIGS. 7 and 8), for engagement with the limb of the patient to which the appliance 10 is being applied. The slip-resistant material 16 as preferably of non-latex and non-allergenic material that has a property of being able to generally adhere to the outer surface of a limb for preventing the primary strap 11 from laterally or longitudinally slipping or creeping or moving along the limb. The slip-resistant material is particularly useful to prevent slippage of the primary strap 11 relative to the limb, due to changes in circumference of the limb or in instances wherein the outer surface of the limb may become slippery due to the presence of such things as hair, perspiration or other influences that might otherwise reduce the ability of the primary strap 11 to retain its intended position along the limb to which it is attached.

The primary strap portion 11 provides the location along the patient's limb at which the catheter or other tube-like member 30 will be secured to the patient's body. Actual securement of the tube-like catheter 30 is provided by means of a secondary strap portion 20. The width of the secondary strap portion 20 may be significantly less than that of the primary strap portion 11, and is in the preferred embodiment, approximately one inch wide. Its length may also vary, but need only be long enough to encircle, as illustrated in FIGS. 2 and 3, the outer circumference of the tube 30 being retained thereby. In the preferred embodiment, the nominal unstretched length of the secondary strap 20 is approximately two inches in length. The secondary strap portion 20 is preferably configured of an elastic webbing material which is stretchable in a longitudinal or lengthwise direction, but which has a relatively fixed width dimension, similar to that of the primary strap 11, but may be significantly thinner material. The "inside" surface of the secondary strap portion 20 is generally indicated at 20a in FIG. 2; whereas the "outer" surface is generally indicated at 20b in FIG. 3. The inner surface 20a of the secondary strap 20 is entirely or partially lined with a layer of slip-resistant material such as silicone, neoprene or latex, generally indicated at 21. The slip-resistant material 21 may either be of solid or ribbed cross-sectional configuration. In the preferred embodiment, the slip-resistant material is of ribbed configuration as illustrated in FIG. 4, wherein the ribs extend longitudinally of the secondary strap 20. In the preferred embodiment, the secondary strap portion material of the preferred embodiment is generally referred to as a woven or knit elastic that is commercially available and will be known to those skilled in the art.

The secondary strap portion 20 is secured (in the preferred embodiment) by stitching 22 to the outer surface 12 of the primary strap 11 toward its second end 11b. The longitudinal length (x) of the secondary strap portion 20 (illustrated in FIG. 2) is preferably equal to or of greater length than the diameter of the tube 30 to be secured, and forms a base or seat for the tube 30 to be secured, as illustrated in FIG. 3. Since the secondary strap portion 20 is of stretchable material, it will stretch with the primary strap portion 11, increasing the "x" dimension as primary strap 11 is stretched when being applied to a limb.

The secondary strap portion 20 extends in unattached manner beyond the leftmost stitching (as illustrated in FIG. 2) toward a distal end 20c that is not secured to the outer surface 12 of the primary strap portion 11. In the preferred embodiment, the length of the secondary strap portion 20 between its distal end 20c end the closest secured stitching 22 as preferably greater than or equal to the "x" dimension of the secondary strap portion, as measured between the spaced stitching 22. A length of an elastic or nonelastic "hook" fastening material 24 is secured by stitching 25 to the outer surface 20b of the secondary strap 20 at its distal end 20c. The hook fastening material 24 is oriented relative to the secondary strap 20 such that its hook-like barbs face in the same direction as the inner surface 20a of the secondary strap 20. In this orientation, when the free or distal end 20c of the secondary strap 20 is folded back toward the secured portion of the secondary strap (as illustrated by the arrow "A" in FIG. 2, and as further illustrated in FIG. 3), the hook members cooperatively address and are permitted to operatively releasably engage the looped outer surface 12 of the primary strap 11. In the preferred embodiment, the width of the fastener 24 is generally the same as that of the secondary strap portion 20, and has a length of approximately 2 to 3 inches, which permits a user of the apparatus to easily grasp and pull on the fastener 24 to stretch the material of the secondary strap 20 around the tube-like member 30 to be engaged thereby as indicated in FIG. 3. However, it will be understood by those skilled in the art, that the dimensions of the fastener 24 as well as those of the other strap portions of the invention, could assume any number of different sized, as dictated by the use to which the appliance 10 will be put.

To secure a catheter or other tube-like member 30 to a limb or other portion of the wearer's body, the primary strap portion 11 is placed around the limb as illustrated in FIG. 1, with the inner surface 13 of the primary strap in engagement with the limb. In such orientation, the slip-resistant material 16 on or forming a proportion of the inner surface 13 will come into direct contact with the outer surface of the limb. The primary strap portion is longitudinally adjusted relative to the limb such that the secondary strap portion 20 attached thereto is aligned with that portion of the limb at which the tube 30 is to be secured. In general, the first end 11a of the primary strap 11 will be held in a fixed position against the limb, while the primary strap 11 is stretched and extended around the outer circumference of the limb by grasping of the primary strap by or adjacent and second and 11b, until the secondary strap portion 20 is in the desired position. At such position, the primary strap 11 will be secured to the limb by engaging the fastener 15 to the outer surface 12 of the primary strap 11, forming a hook and loop fastener system, as is well-known in the art. Due to the presence of the slip-resistant material 16 along the inner surface of the primary strap 11, the primary strap 11 will thereafter remain in the position in which it was affixed to the limb.

The tube 30 to be secured by the appliance is placed across and seated upon the secured length "x" of the secondary strap 20 and against the slip-resistant material 21 thereof as illustrated in FIG. 3. The tube 30 as secured, as positioned, to the primary strap 11 by pulling on the fastener 24 so as to longitudinally stretch the unsecured portion of the secondary strap 20 and by folding and entraining the stretched secondary strap 20 back over the tube 30 to form a loop which compressably encircles the loop 30, and by securing the fastener 24 to the outer surface 12 of the primary strap 11 soas to retain the stretched condition of the secondary strap 20, as illustrated in FIGS. 1 and 3. In such position, the secondary strap 20 will firming retainable engage and hold the tube 30 in position against the primary strap 11 as illustrated in FIG. 1, without crimping, bending or damaging the tube 30. The elasticity of the secondary strap 20 and the frictional engagement of its slip-resistant lining 21 provides snug retaining engagement of the tube 30, but allow the tube 30 to be manually adjusted in its longitudinal direction after fastening, if so desired.

Due to the relatively short length of the secondary strip portion 20, the secondary strap fastener 24 will engage the primary strap 11 in close proximity to the retained tube 30, thereby forcing the proximal end of the secondary strap toward retaining engagement with the tube. With this configuration, approximately two-thirds or more of the outer circumferential area of the tube 30 is engaged by the slip-resistant material 21 of the secondary strap, providing a secure, yet safe engagement of the tube.

It has been found that the above-described configuration of the appliance, having a primary strap with slip-resistant material on its inner surface, provides significant improvement over prior art structures in maintaining the desired operative position of the appliance relative to a limb of the wearer. The invention has been found to be particularly effective for use on limbs that have a tapered, frusto coxical configuration or which have a tendency to change shape or configuration such as muscular or fleshy limbs, or ones which include friction reduced surfaces—all of which have a tendency to enhance slippage or creep to straps or appliances attached thereto. Such position retention not only provides added comfort to the wearer of the appliance, but helps to maintain the intended positioning and operation performance of the catheter or other elongate structure being held thereby.

While the invention has been described with respect to its application as illustrated in the preferred embodiment, it will be understood that a number of variations of such embodiment and its applications for use with devices other than a catheter or tube-like structures, are possible. Other modifications of the invention will become apparent to those skilled in the art in light of the foregoing description. This description is intended to provide specific examples of embodiments which clearly distinguish and disclose the principles of the invention, but are not intended to represent limitations on the scope of the invention. All alternatives, modifications and variations of the present invention that fall within the broad scope of the appended claims are intended to be covered by this invention.

The above specification, examples and data provide a complete description of the manufacture and use of the composition of the invention. Since many embodiments of the invention can be made without departing from the spirit and scope of the invention, the invention resides in the claims hereinafter appended.

We claim:

1. An appliance for anchoring a catheter or other tubular device to a body portion of a person, comprising:
   (a) a primary strap member configured to encircle the body portion to which said catheter is to be retained, said primary strap member having oppositely disposed outer and inner surfaces;
   (b) a fastener system for releasably securing said primary strap member around and into snug engagement with said body portion; wherein said inner surface of said primary strap member cooperatively addresses said body portion;
   (c) a plurality of spaced lengths of silicone material adhered to said inner surface and extending above the general plane of said inner surface soas to engage said body portion and provide a slip-resistant extension of said inner strap surface; and
   (d) a secondary member secured to said primary strap member, configured to releasably secure an elongate object to said primary strap member.

2. An appliance as recited in claim 1, wherein said fastener system comprises a hook and loop fastening system.

3. An appliance as recited in claim 1 wherein at least those portions of said appliance that are designed to contact said body portion comprise non-allergenic materials.

4. An appliance as recited in claim 3, wherein said non-allergenic materials contain no latex.

5. An appliance as recited in claim 1, wherein said beads of silicone material are configured in an open pattern along said inner surface of said primary strap member.

6. An appliance as recited in claim 1, wherein said primary strap member is at least partially configured of stretchable material allowing said primary strap material to stretch in its longitudinal direction.

7. The appliance as recited in claim 6, wherein said silicone material is stretchable material that stretches with said primary strap member, while retaining portions thereof that extend above the general plane of said inner surface.

8. The appliance as recited in claim 1, wherein said primary strap member comprises breathable material enabling air passage between said outer and inner surfaces thereof.

9. An appliance as recited in claim 1, wherein said silicone comprises shaped beads of silicone material.

10. An appliance as recited in claim 1, wherein said silicone material occupies less than about 50% of said inner surface.

11. An appliance as recited in claim 10, wherein said silicone material occupies less than about 25% of said inner surface.

12. An appliance as recited in claim 10, wherein said silicone material comprises less than about 10% of said inner surface.

13. An appliance as recited in claim 1, wherein said primary strap material is porous to air passage through said first inner surface, whereby the limb engaged by said primary strap member is enabled to breathe through said primary strap member.

14. An appliance as recited in claim 1, wherein said plurality of spaced lengths of silicone material are configured in spaced patterns of silicone material longitudinally extending along the inner surface of said primary strap member.

15. The appliance recited in claim 14, wherein said spaced patterns are continuous curved patterns.

* * * * *

UNITED STATES PATENT AND TRADEMARK OFFICE
CERTIFICATE OF CORRECTION

PATENT NO. : 6,645,185 B2
DATED : November 11, 2003
INVENTOR(S) : Bird et al.

It is certified that error appears in the above-identified patent and that said Letters Patent is hereby corrected as shown below:

Column 2,
Line 34, "and does require" should read -- and does not require --

Column 6,
Line 13, "primary strap ii" should read -- primary strap 11 --

Column 10,
Lines 30-31, "through said first inner surface," should read
-- through said inner surface, --

Signed and Sealed this

Fourth Day of May, 2004

JON W. DUDAS
*Acting Director of the United States Patent and Trademark Office*